and Method for

United States Patent [19]
Danby et al.

[11] Patent Number: 4,929,329
[45] Date of Patent: May 29, 1990

[54] ELECTROPHORESIS CASSETTE SYSTEM WITH APPARATUS AND METHOD FOR FILLING SAME

[75] Inventors: Philip C. Danby, Chestnut Hill, Mass.; Hal C. Danby, Sudbury, England; Eric R. Hungerman, Woburn, Mass.

[73] Assignee: EG&G, Inc., Wellesley, Mass.

[21] Appl. No.: 127,655

[22] Filed: Dec. 2, 1987

Related U.S. Application Data

[63] Continuation-in-part of Ser. No. 43,212, Apr. 27, 1987, abandoned.

[51] Int. Cl.$^5$ ............................................. G01N 27/26
[52] U.S. Cl. ................................. 204/299 R; 204/182.8
[58] Field of Search ............. 204/299 R, 182.8, 182.9, 204/180.1

[56] References Cited

U.S. PATENT DOCUMENTS

| | | |
|---|---|---|
| 3,432,414 | 3/1969 | Rand . |
| 4,339,327 | 7/1982 | Tyler ............................... 204/299 R |
| 4,417,967 | 11/1983 | Ledley . |
| 4,524,769 | 11/1986 | Simada et al. . |
| 4,576,693 | 3/1986 | Kreisher et al. . |
| 4,762,743 | 8/1988 | von Alven et al. . |

FOREIGN PATENT DOCUMENTS

2180941 A  4/1987  United Kingdom .

OTHER PUBLICATIONS

A. C. Arcus; "Vertical Gel Electrophoretic Analysis in Slabs: A Simple Apparatus" Laboratory Practice, Apr. 1976.
Instruction Manual for "Poker Face" Sequencer, SE 1500, Hoffer Scientic Instruments, 1985.
Gel Electrophoresis of Nucleic Acids; Edited by D. Rickwood and B. D. Hanes; pp. 39–41, 81–85, 88; I. R. L. Press; Oxford, England; 1982.
Bethesda Research Laboratories Brochure Entitled "Priceless Performance, Affordable Price" 1984.

*Primary Examiner*—John F. Niebling
*Assistant Examiner*—John S. Starsiak, Jr.
*Attorney, Agent, or Firm*—Wolf, Greenfield, & Sacks

[57] ABSTRACT

An electrophoresis cassette system which when used with a detector can automatically perform an analysis of radio-labelled molecules. The cassette system is easily assembled and may be reused. The cassette includes a new type of side spacer which incorporates nylon monofilament and which includes a buffer zone for increased accuracy. A new clamp and other improvements further enhance the accuracy of the cassette and reduce variations in the electric field at the bottom and sides of the cell to provide increased accuracy. A new cassette filling system is shown for use with the cassette which permits rapid filling of a cassette with gel material while providing a more uniform gel layer than was previously attainable.

36 Claims, 6 Drawing Sheets

ELECTROPHORESIS CASSETTE SYSTEM WITH APPARATUS AND METHOD FOR FILLING SAME

This application is a continuation-in-part of Ser. No. 43,212, filed Apr. 27, 1987, now abandoned.

FIELD OF THE INVENTION

The present invention is related to electrophoresis systems, and in particular to an electrophoresis cassette system and detector for performing automatic sequencing of biological macramolecules, such as DNA and RNA.

BACKGROUND OF THE INVENTION

Proteins and other large biological molecules, including DNA, may be separated for analysis using electrophoresis techniques. One particularly important application of these techniques is the sequencing of the DNA and RNA molecules. In performing an electrophoresis separation of such molecules, a gel is formed between two non conducting plates, such as glass, to form a thin sheet of gel between the glass surfaces. The gel should be as uniform in thickness and other properties as possible. The surfaces at either end of the gel are each connected to a buffer reservoir which serve as electrodes. A potential is applied across the gel by connecting each reservoir to opposite polarities of a voltage source.

The collection of molecules to be sorted is placed at the negative electrode end of the gel, usually in preformed wells. The molecules are negatively charged, and the electric field in the gel reacts with the charge on the molecules to provide a force propelling the molecules through the gel towards the positive electrode. Smaller molecules have less resistance to traveling through the gel than larger molecules, resulting in a separation and sorting of the molecules by size as they migrate through the gel.

Synthesis of fractional lengths of DNA (or RNA) molecules by means of enzymes allows the molecule to be analyzed according to the sequence of bases making up such a molecule. Techniques for doing this type of analysis are well known. See for example Sanger, F., S. Nicklen & A.R. Coulson 1977 Proc. Natl. Acad. Sci. USA 74: 5463–5467; Prescott L. Deininger Analytical Biochemistry 135, 247 263 (1983); Garoff, H., & Ansorge, W. (1981) Anal. Biochem. 115, 450 457; and Biggin, M.D., T.J. Gibson & A.F. Hong 1983 Proc. Natl. Acad. Sci. USA 80: 3963–3965.

One method employed to view the electrophoretic separation of macromolecules in a gel involves radiolabelling the molecules. Typically, the gel used for electrophoresis is removed from its cassette and placed alongside a photographic medium which is exposed by the radioactive emissions of the radio-labelled molecules. Developing the emulsion produces a series of stripes representative of the position of each set of macromolecules in the case of sequencing their relative locations can be used by the investigator to derive the base relative locations sequence directly. This type of analysis requires a high degree of training, is time consuming, tedious and very prone to transcription errors. Automatic detection methods have been proposed in which detectors responsive to the radioactive emission are used to automatically perform DNA sequencing. However, due to variations from the ideal operation of the electrophoresis gel cassette, automatic systems have not performed well.

A system which is capable of performing an electrophoresis separation of macromolecules in such a way that relatively simple detection apparatus can reliably and accurately determine their position would have great advantages. Additionally, current methods for assembling gel cassettes for performing electrophoresis require great skill and considerable time. A gel cassette which could be assembled and loaded with gel by a relatively unskilled technician while retaining the above mentioned features would greatly aid in performing electrophoresis analysis of biological macromolecules.

SUMMARY OF THE INVENTION

The present invention includes an electrophoresis cell and accompanying detector which can automatically perform an analysis of radio-labelled molecules The present invention is particularly suitable for analysis of DNA (RNA) molecules, but is also useful in the electrophoresis separation and analysis of other substances. The present invention includes a novel gel cell in which the electric field is maintained much more uniformly then in prior art cells. The cell includes a novel method of separating the plates between which the gel is formed. A novel well configuration at the top of the gel, a new plate clamp, and other improvements further enhance the accuracy of the cassette and reduce variations in the electric field at the bottom and sides of the cell to levels which do not affect the field. Additionally, a new cassette filling system is shown which permits rapid filling of a cassette with gel material which is faster than previously known methods and which provides a more uniform gel layer.

DESCRIPTION OF THE DRAWINGS

The advantages and operation of the present invention will become more clear upon the reading the following description of the preferred embodiment in conjunction with the accompanying drawings of which:

FIG. 16 shows a prior art window construction for use with detectors for radio-labelled material;

FIG. 17a, 17b, & 17c shows the collimator assembly used in the present invention;

FIG. 18 illustrates how the groove may be formed in a glass plate for locating a collimator; and FIG. 19 illustrates a novel method and apparatus for filling a gel cassette of the present invention;

FIGS. 20 and 21 show details of the filler locking mechanism;

FIG. 22 shows details of the filling block;

DESCRIPTION OF THE PREFERRED EMBODIMENT

Figure 1:
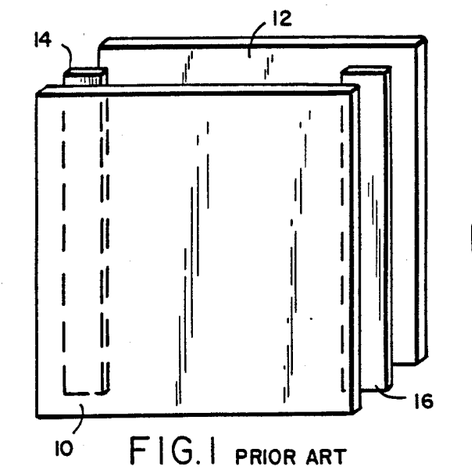
FIGS. 1, 2, 2a, 3, & 4 illustrate the construction of a typical prior art gel cassette.

Referring to FIGS. 1–4, there is shown a typical prior art gel cell or cassette used for electrophoresis separation of DNA and RNA molecule fragments. Referring to FIG. 1, two flat plates 10 and 12 are brought together facing one another and separated by side spacers 14 and 16. The front and back plates should be made of a flat, non porous insulator which does not react with the gel material or the molecules being analyzed. Typically, plates 10 and 12 are formed of glass. Front and back plates are typically on the order of 12 inches by 12 inches.

Separators 14 and 16 are placed between the front and back plates 10 and 12 when they are assembled to form a uniform gap between the plates in which the gel is placed. The spacers determine the gel thickness and are on the order of 0.010 to 0.020 inches thick. Spacers 14 and 16 are on order of $\frac{1}{4}$" wide and are typically formed from a sheet of mylar or other suitable material.

To form the gel layer, the components in FIG. 1 are brought together as described above. The front and back glass plates 10 and 12 are spaced apart by the side spacers 14 and 16. The edges of front and back plates 10 and 12 are clamped together so that the gel material which will be inserted between the plates cannot escape through the sides. A strip of tape is usually placed along the bottom of the gel cell to provide a seal. The gel is then formed between front and glass plates in the following manner.

A suitable material such a polyacrylamide or agarose gel is used to fill the space between plates 10 and 12. These materials are liquid when they are poured or injected between the plates, after which the materials solidify to form a gel. It is essential for the proper operation of the electrophoresis separation that the gel be absolutely uniform. Any imperfection in the gel will affect the speed and direction of the molecules diffusion under the influence of the electric field applied to the gel. Imperfections may be caused by air bubbles or dust within the gel and by other factors, as discussed below.

Learning how to construct and assemble an electrophoresis gel cassette usable for sequencing takes a great deal of training and practice. Even with experienced assembly, many cassettes formed in the conventional manner will have defects and other imperfections which will cause the separation to take place in an unpredictable way.

Figure 2:
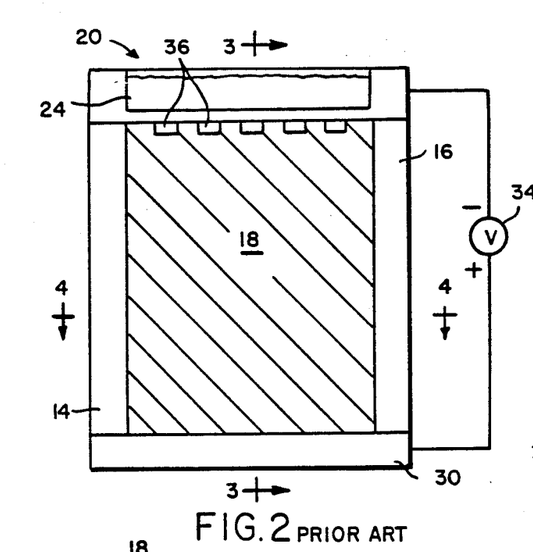
Figure 3:
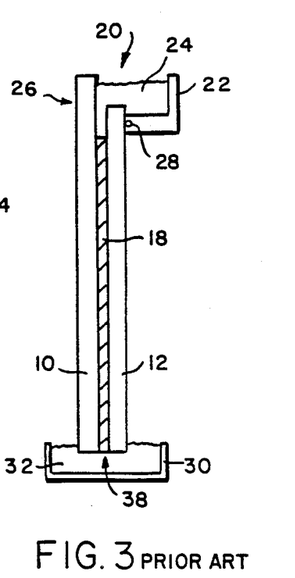
Figure 4:
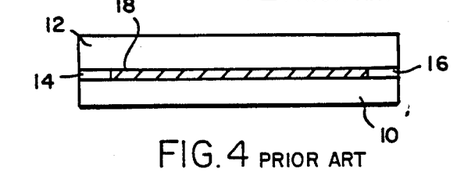

FIG. 2 illustrates a typical electrophoresis system using a gel cassette of the type discussed above in connection with FIG. 1. In FIG. 2, which is a front view of the cassette, the gel material 18 is contained between front and back plates 10 and 12. FIG. 4 is cross-sectional view through the cassette shown in FIG. 2 at the location illustrated by section line 4—4. FIG. 3 is a cross sectional view of the gel cassette along the vertical plane illustrated by section line 3—3.

A reservoir 20 containing a buffer solution 24 is formed at the top of the cassette to provide an electrical connection to the top of the gel material 18. Typically, the reservoir is formed between an upper extension 26 of the front glass plate 10 and a rear piece 22 which forms the floor and sides of the rear of the reservoir. A tubular gasket 28 is clamped between the reservoir extension 22 and the back of the gel cassette, by means of clamps not shown in the figures to provide a seal.

The bottom of the gel cassette is immersed in a bottom reservoir 30 containing a second buffer solution 32 which provides electrical contact with the bottom of the gel layer 18. A voltage source 34 is electrically connected between the top buffer solution 24 and the bottom buffer solution 32. Typically, the voltage from voltage source 34 is on the order of 1000 volts. The electric potential between the top and bottom buffer solutions induces an electric field within the gel layer 18. The objective is to provide a completely uniform electric field within the gel layer 18 having equipotential lines which are exactly parallel to the horizontal extent of the gel layer.

Figure 2A:
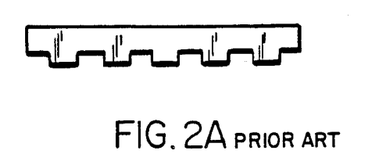

Normally, electrophoresis of several collections of molecules are run through the gel at the same time. In FIG. 2, a plurality of wells 36 is formed in the top of the gel layer 18. A collection of molecules to be separated is injected into each of the wells by means of a hypodermic needle small enough to fit in the narrow opening between the front and back plates 10 and 12 of the gel cassette. Wells 36 may be formed by means of a piece of the same material from which the sides spacers 14 and 16 are formed, which is cut in the proper shape to form the well configuration shown in FIG. 2. This piece is called a "comb ." The comb is inserted after the liquid gel solution has been poured and before the gel hardens. After the gel has hardened, the comb is removed to leave the wells in which the molecules to be analyzed are placed. FIG. 2A illustrates the configuration of a comb 36 which could be used to make the wells shown in FIG. 2.

While the desired uniform field in gel 18 would appear to result from the above-described construction shown in FIG. 2, in actual practice, such is not the case. It has been found that conventional gel cassettes suffer from imperfections which result in non uniform fields within the gel layer 18.

The two primary sources of irregularities in the field are that the side boundaries of gel layer 18 are not perfectly straight and the thickness of the gel is not uniform. Ideally, the gel layer 18 is constrained by side spacers 14 and 16 so that the boundaries are straight, parallel, vertical, as shown in FIG. 2. The liquid from which the gel is formed, however, has a high capillarity, and will tend to wick into any small space with which it comes in contact. Due to small variations in the thickness of the spacer 16 and the flatness of front and back plates 10 and 12, contact between the side spacers 14 and 16 and the front back plates 10 and 12 is not uniform. The result is that gel solution may get into small spaces between the side spacers and the glass plates producing an irregular side edge to the gel layer 18. Dust particles may also get into this area causing additional spaces into which the gel material may flow. Attempts to decrease the leaking by applying more clamping pressure can cause the glass plates to distort causing uneven gel thickness and a consequent distortion of the electric fields. Additionally, the bottom surface 38 of the gel material is not perfectly flat after the tape sealing the bottom of the gel cassette is removed. These variations also contribute to a non-uniform electric field.

The seal between the back wall 22 forming reservoir 20 and the glass plates 10 and 12 may also contribute to irregularity in the electric field. If the seal provided by tubular gasket 28 is not perfect buffer solution leaks outside the gasket. Applying more force to clamp the gasket 28 more tightly between the reservoir wall 22 and the glass plate may well result in a bending or warping of the glass plate which will further contribute to non-uniformity of the electric field.

Figure 5:
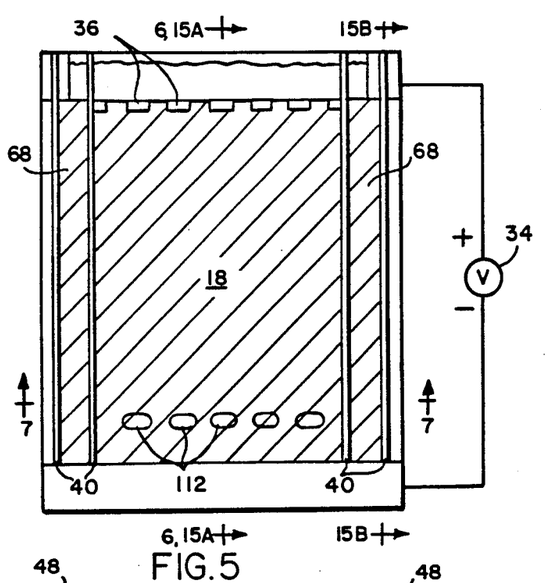
FIGS. 5–7 show the cassette of the present invention.
Figure 6:
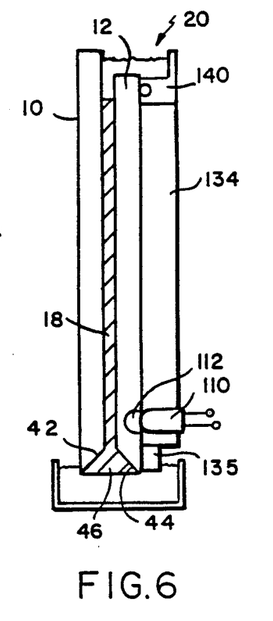
Figures 7, 8A, 8B, 9A, 9B, 9C:
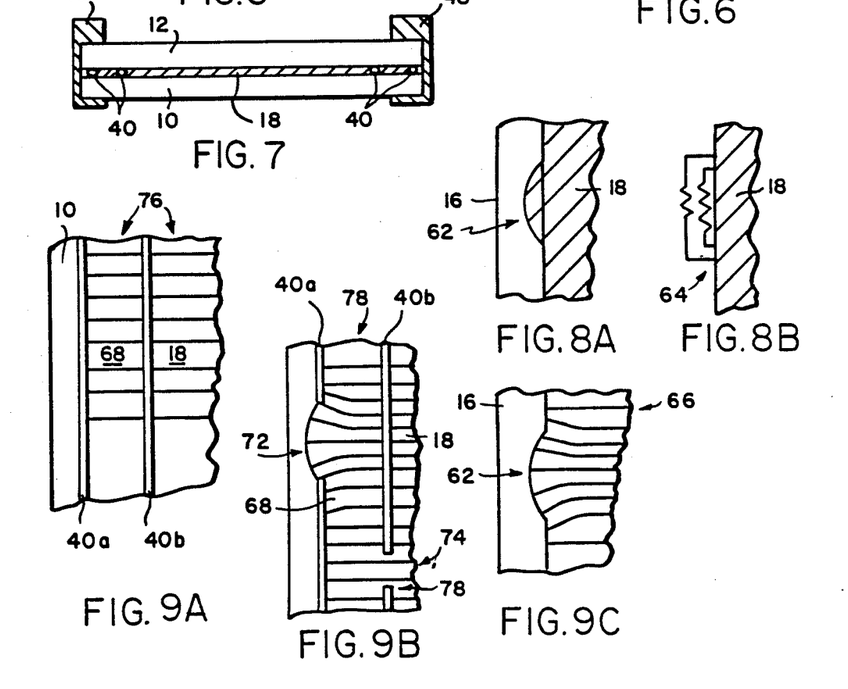
FIG. 8a & 8b shows variations in the electric field of a prior art cassette which result from a leak in the gel cell boundary.
FIG. 9a, 9b & 9c shows electrical field variations in the present invention which result from a leak in the gel cell boundary.

Referring to FIG. 5, 6, and 7, there is shown a new gel cassette and electrophoresis system constructed in accordance with the present invention which reduces or eliminates the irregularities in the electric field typical of prior art cassettes. FIG. 5 is a front view of the electrophoresis system. FIG. 6 is a side view taken through a plane denoted by section lines 6—6 in FIG. 5, and FIG. 7 is a top view taken at a plane denoted by section line 7—7 in FIG. 5.

In FIG. 5, a gel layer 18 is formed between front and back plates 10 and 12 as in a conventional cassette. Front and back plates 10 and 12 are spaced apart from one another by means of spacers 40 which provide a line contact between each of the spacers and the front and back plates 10 and 12. In the preferred embodiment, spacers 40 are constructed from nylon monofilament. Two spacers 40 are provided on each side of the gel layer 18 for reasons discussed below.

It has been found that the use of monofilament line has many advantages over the use of flat spacers such as 14 and 16 discussed above. Monofilament is readily available inexpensively and in quantity in a selection of diameters. The diameter of monofilament is typically maintained within a tolerance similar to that of mylar or other plastic sheeting commonly used for side spacers in prior art cassettes. It has been found that the uniformity of 0.010" diameter monofilament is typically within approximately one ten thousand of an inch.

More importantly, the monofilament spacers contact the front and back plates 10 and 12 along a very thin line to provide what is essentially a line contact. This has several beneficial results. First, dust does not tend to become trapped between the spacer and the glass plate. The very small area over which the spacers contact the glass greatly reduce the area over which dust particles will produce gaps. Additionally, the circular shape of the monofilament will tend to push a dust particle aside rather than allowing the dust particle to create a space between the monofilament and the plate.

It should be appreciated that materials other than nylon monofilament may be used to form the spacers of the present invention. Although not as easily manufactured, spacers having an elliptical cross section are capable of providing the desired point contact seal. Even a polygonal cross section, such as an octagon, will distribute the clamping force over a very small area and provide a seal which is substantially equivalent to the point contact seal desired. Materials other than nylon may be used for fabricating the spacers. The primary requirements of the spacers are that they are slightly resilient, flexible, and have very small tolerance for the dimensions of the spacer cross section.

The force clamping the front and back plates 10 and 12 together is distributed over a much smaller area by the monofilament spacers 40, resulting in much better conformation between the spacers and any surface irregularities in the glass plates. Thus, smaller forces are required to provide an adequate seal between the spacers 40 and the glass plates. As will be explained in more detail below, the use of 2 monofilaments spacers on each side of the gel layer 18 greatly reduces or eliminates variations in the electric field due to leakage past these spacers.

The uniformity of the sealing provided by monofilament spacers 40 is enhanced by the use of novel side clamps 48, not shown in FIGS. 5 and 6, to hold the front and back plates 10 and 12 in contact with spacers 40. These clamps run the entire length of the gel cell from the bottom to the top of plates 10 and 12. The location of clamps 48 is illustrated in FIG. 7. The construction of these clamps is shown in more detail in FIG. 14.

Figures 13, 14, 15C, 23:
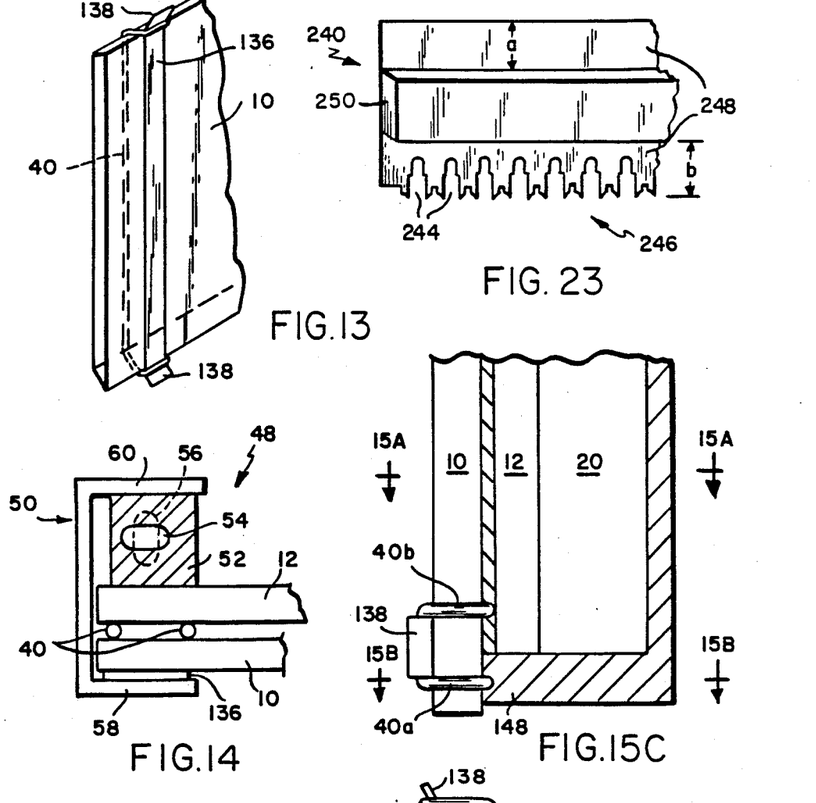
FIG. 13 shows one method by which the monofilament spacers in the present invention may be attached to a glass plate.
FIG. 14 shows details of the novel side clamp of the present invention.
FIG. 15a, 15b, & 15c shows the configuration of the upper buffer reservoir in the present invention and its attachment to the cassette glass plates.
FIG. 23 shows an alternate comb for forming indentations in the gel material for separating samples to be analyzed.

Referring to FIG. 14, a clamp support piece 50 is formed from a channel-shaped piece of material, typically a machined piece of acrylic, which runs the entire length of the gel cassette. A first side 58 of the channel bears against the front face of glass plate 10 through a plastic shim strip 136. A rubber locking piece 52 bears against the opposite face of the gel cassette on glass plate 12. The rubber piece 52 has a square outside configuration and also runs the length of the gel cassette. Rubber piece 52 is held against the back face of the cassette by the second side 60 of the channel piece 50.

An oval shaped opening 54 is formed in the rubber piece 52 and goes thru the length thereof. The longer dimension of opening 54 is parallel to the back face of glass plate 50. To clamp the gel cassette together, a solid, oval-shaped tensioning rod is put into hole 54 for the entire length of the rubber piece. The rod is then twisted 90 degrees until it has the orientation shown by dotted lines 56 in FIG. 14. In this manner, a uniform pressure may be quickly and easily applied to the front and back plates 10 and 12 across the locations of monofilament spacers 40.

The clamping system shown in FIG. 14 provides a uniform force along the monofilament spacers so that there is sufficient pressure to ensure sealing. Since the distribution and total amount of force is determined by the clamp design and not by the user, distortion of the glass due to overtightening of the clamps or uneven clamping forces is eliminated. It should be appreciated that materials other than rubber may be used for the resilient piece 52 and that the opening 54 and tensioning rod may have shapes other than ovals.

Another feature of the present invention which contributes to the uniformity of the electric field is shown in FIG. 6 wherein the bottom edge of either or both of the glass plates 10 and 12 is bevelled to provide a wedge shaped base to the gel layer which has a much lower electrical resistance than the remainder of the gel layer. This is shown in FIG. 6 where bevels 42 and 44 at the bottom of plates 10 and 12 provide a wedge 46 of gel. Due to the much lower resistance of gel wedge 46, unevenness in the bottom surface of the gel affects the electric field much less.

For example, a typical gel layer is 0.010" thick while the glass plates 10 and 12 are typically on the order 0.100" thick. The conductivity of the gel layer is directly proportional to its thickness, and the reduction in the resistance at the bottom of the gel wedge 46 is proportional to T/t, where T is the thickness at the bottom of gel wedge 46 and t is the thickness of the main body of the gel. Thus, the resistance at the bottom layer of the gel wedge 46 is on the order of 20 times less than the main body of the gel layer. As a result, the effects on the electric field of variations in the smoothness of the bottom of the gel layer are reduced by a factor of 20.

As discussed above, the spacer configuration shown in FIG. 5 has significantly better performance than do prior art electrophoresis cells using flat spacers. The reason for this may been seen referring to FIGS. 8 and 9. In FIG. 8, a portion of the side of a prior art gel cassette using plastic strip type spacers 16 is shown. In FIG. 8A, an imperfection in the seal between the spacer 16 and the front end glass plates is illustrated at position 62. As a result, the gel material 18 flows into the area where the seal is not complete, as shown in FIG. 8A.

Referring to FIG. 8B, resistors 64 represent the electrical equivalent of the situation shown in FIG. 8A. A shunt resistance, represented by resistors 64, is effectively connected along the side of a portion of the gel cassette where the seal imperfection is located. In the presence of a leak in the seal, current will flow through the extra gel material extending sideways from the normal gel boundary. This current distorts the electric field in the gel in the area adjacent to the unsealed area, which will affect the path of molecules diffusing through the gel under the influence of the applied electric potential. This is shown in FIG. 9C where lines 66 represent the equipotential lines which result from a leak 62 in the side seal 16. The exact configuration of the equipotential lines will vary, depending on the size and shape of the seal imperfection. However, any seal leak will produce a significant effect on the electric field in the vicinity of the seal.

The dual monofilament spacer configuration shown in FIG. 5 significantly reduces problems of the sort illustrated and discussed above in connection with FIG. 8 for two reasons. First, as discussed above the seal provided by monofilament spacers 40 is much better than the typical seal provided a flat plastic spacer 16. Second, the use of two monfilament spacers on each side creates a buffer zone 68 which reduces the effects of any gaps which may exist in the seal. This is shown more clearly in FIG. 9.

Referring to FIG. 9A, a portion of the side seal along a gel cassette is shown. In FIG. 9A, the outside monofilament spacer 40a and the inside monofilament spacer 40b both provide a perfect seal. The resulting equipotential lines resulting in the gel material in the main cassette body 18 and in the buffer zone 68 are straight lines perpendicular to the vertical direction of the gel cassette.

Referring to FIG. 9B, a similar section of a gel cassette of the present invention is shown in which there are two defects in the seal provided by the monofilament spacers 40. A gap 72 is shown in the seal provided by outside spacer 40a and the second gap 74 is shown in the seal provided by inside spacer 40b. Although gaps may and do occur occasionally in the seal provided by monofilament spacers, the chances are low that a gap in the inside spacer seal will occur adjacent to a similar gap in the seal provided by the outside spacer 40a.

If there is a gap in the seal provided by the outside spacer 40a, some of the gel material will bulge outwardly from the buffer zone 68, as shown at location 72. This will affect the field in the buffer zone gel. However, if the inside seal opposite the gap 72 is intact, the deviation of the field in the main body 18 of the gel will be negligible, as shown by the equipotential lines in FIG. 9B.

FIG. 9B also shows a gap 74 occurring in the seal provided by the inside spacer 40b. In this case, if the outside seal provided by spacer 40a is intact in the vicinity of the gap 74 in the inside seal, there will be no effect on the electric field in the main body 18 of the gel cassette, as shown by equipotential lines 78 in FIG. 9B.

Even in the case where gaps in the inside seal and outside seal are adjacent to one another, the buffer zone 68 provided by the two monofilament seals 40 attenuates the effect on the electric field within the main body 18 of the gel cassette which will result from such leaks. The net effect on the electric field in the main body of gel cassette 18 from adjacent gaps in the inner and outer seals will be significantly less than the effect on the field produced by a similar leak with a strip type spacer used in the prior art.

It should be noted that the use of a buffer zone 68 to reduce the effects on the electric field of leaks in the spacers are a function and a result of the point contact seal provided by monofilament spacers 40. A similar buffer zone could not reasonably be implemented by using multiple flat spacers 16. Referring to FIG. 8A, an imperfection in the seal when using a flat spacer 16 will generally result in an irregular area 62 which contains gel material. Due to the electric field in the gel, a current will flow in this irregular area. In order for the current to flow sideways into the area, the field lines must deviate from the desired vertical orientation. Even if the leak in the strip spacer extends entirely through the spacer, non-vertical components in the electric field must exist in order for the current to flow into and out of the seal imperfection area. In the present invention, the seal has negligible width, and thus the deviations from the desired electric field caused by current flowing in the area around a seal imperfection are greatly reduced or eliminated.

Monofilament spacers 40 may be located and maintained in placed in the following manner. Referring to FIG. 13, a section of front plate 10 is shown which illustrates the mounting of monofilament spacers 40. A stiff, resilient strip 136 of material which is equal in length to the height of glass plate 10 is placed along the front surface of the plate. The top and bottom ends of strip 136 end in two short tabs 138 which project out at an angle from the front face of glass plate 10. This may be seen more clearly in FIG. 15B. Strip 136 and tabs 138 are made of a PVC material in the preferred embodiment. If desired, strip 136 may be attached to the front of glass plate 10 with an adhesive. This contributes to the speed and facility with which the monofilament spacers may be replaced when reassembling and filling a new gel cassette. The width of the spacer 136 is preferably wide enough so that it distributes the pressure from clamp 50, discussed below, across that portion of front plate 10 which bridges the space between monofilament spacers 40, as shown in FIG. 14.

A loop of monfilament is formed by crimping the ends of a piece of monofilament together. The loop is then placed over one of the tabs 138, wrapped around the back (inside) side of plate 10, and looped over the top of the other tab 138. The monofilament material is elastic enough to allow this to be easily accomplished while providing sufficient tension to retain the monofilament spacers securely in place.

The point at which the loop is formed by crimping the monofilament ends together should be located somewhere other than on the inside surface of plate 10, since the crimping operation will distort the monofilament diameter. If desired, grooves may be formed in the top and bottom edges of plate 10 to further locate and secure the monofilament spacers. Additionally, placement of the spacers 40 may be facilitated by attaching nylon tabs to the loop at the points where it passes over mounting tabs 138 on strip 136. In this manner, the monofilament spacers may be securely positioned during assembly. This method has the additional advantage that the monofilament loop may be removed and replaced to provide new spacers if and when the cassette is reused.

Another feature of the present invention which contributes to the maintenance of a constant field within the main body 18 of the gel cassette is the configuration of the wells 36 at the top of the gel material. The conventional manner of forming wells 36 in the top of a gel cassette is shown in FIGS. 2 and 2A.

Figure 10:
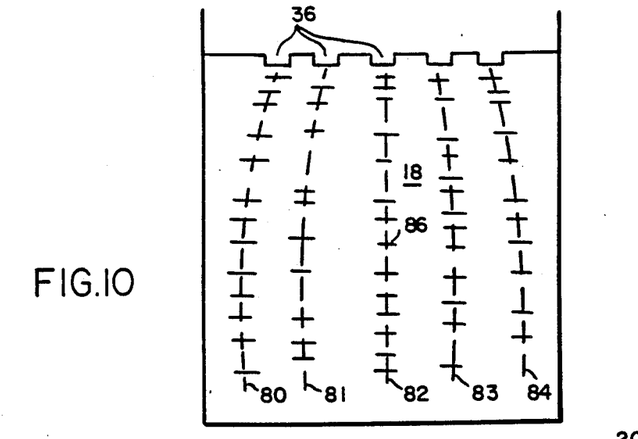
FIG. 10 shows the lateral spreading in the lane of a typical prior art gel cell.

In FIG. 2, a plurality of wells 36 are formed which extend into the gel material 18. The resulting paths of materials put into such wells is shown in FIG. 10. In FIG. 10, a plurality of wells 36 is formed in the top of the gel 18 of a prior art gel cassette. Molecules diffuse downwardly from each of the wells under the influence of the electrical field. The paths followed by the molecule are referred to as lanes. In FIG. 10 the materials diffusing down the individual lanes of the gel cassette will follow the paths denoted by dotted lines 80–84. Horizontal lines 86 represent the final location of the molecule segments after an electrophoresis run has been performed. As can be seen from FIG. 10 the outside lanes 80 and 84 are deflected toward the outside of the gel cassette and have a pronounced curve. This effect is lessened but still exists for lanes further from the sides of the gel cassette, as illustrated by lanes 81 and 83 in FIG. 10.

Figure 11:
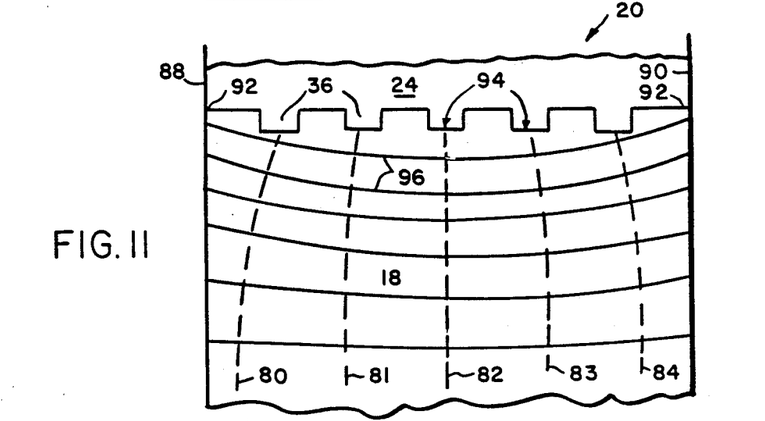
FIG. 11 illustrates the curving of equipotential lines resulting from the formation of wells in a typical prior art gel cassette.

The explanation of this lane track distortion may be seen by referring to FIG. 11. The electrical connection to the top of the gel material 18 in a gel cassette is made through the liquid of the buffer solution 24 in the top reservoir 20. The resistance of the buffer solution is much less than the resistance of the gel material 18. Consequently, the reservoir may be approximated to be an area of equipotential located along the top of the gel material. The formation of wells 36 in the top of the gel material is typically done in a manner so that the height of the gel adjacent to the side boundaries 88 and 90 is equal to the top of wells 36.

Since the reservoir is essentially an electrode of constant potential, the voltage at locations 92 at the top edge of the gel cell adjacent to the side boundaries is the same as the voltage at the bottom surfaces 94 of each of the wells 36. As a result, the equipotential lines beneath the well are curved as shown by lines 96 in FIG. 11. The molecules will diffuse along the field lines which are perpendicular to the equipotential lines. Thus, molecules starting from wells will follow the path shown by the dotted lines 80–84 in FIG. 11, producing the above described distortion in the lane.

Figure 12:
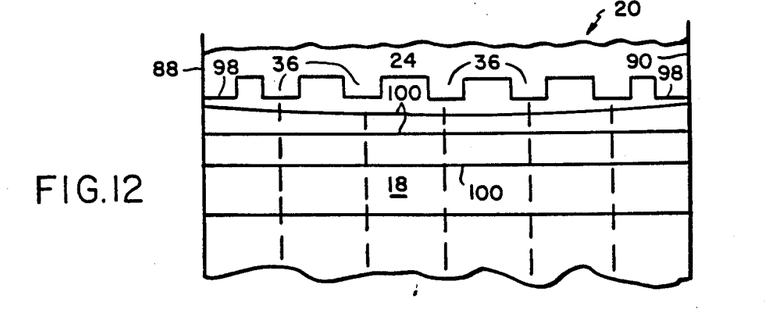
FIG. 12 shows the method of forming wells in the present invention and the equipotential lines resulting therefrom.

In FIG. 12, an alternate configuration is shown for the top of the gel material 18. In FIG. 12 a plurality of wells 36 is formed in the top of the gel material 18, similarly to FIG. 11. In FIG. 12, however, two additional spaces or side wells 98 are formed in the gel adjacent each of the side boundaries 88 and 90. These spaces are similar to wells 36 but molecules for diffusion are not injected into these spaces. The bottom of the spaces 98 are at the same potential as the bottoms of the wells 36. Since the bottoms of the spaces 98 and wells 36 are all in the same plane, the resulting field lines are much straighter, as indicated by field lines 100 in FIG. 12.

It should be appreciated that the equipotential line shown in FIGS. 11 and 12 are rough approximations of the actual field. In particular, fringing fields in the areas between each of the wells 36 will have very complicated configurations. However, the effects of fringing fields diminish rapidly as the distance from the wells increases, and the equipotential lines shown in FIGS. 10 and 11 illustrate the electric field forces which cause lane tracking distortion in prior art electrophoresis system. The exact depth of side wells 98 for the best performance will vary depending upon the particular configuration of wells formed in the top of the gel. It has been found that adding side wells 98 having a depth of 50% to 100% of the depth of molecule wells 36 provides the best results. These side wells may be formed simultaneously with the formation of molecule wells 36 by means of a comb similar to that shown in FIG. 2A but modified to produce side wells 98.

As a result of the improvement in the electric field provided by the various aspects of the present invention discussed above, molecules will diffuse in paths which are very close to the desired vertical straight line paths. The present invention may be used with equipment which will automatically detect molecules diffusing through the gel. In particular, detectors for responding to radiation from radio-labelled molecule segments may be used to automatically detect the passage of such molecule segments.

An alternate method for isolating samples is as follows. A gel cassette is assembled and filled with gel material as described above, except that the gel is formed with a flat top surface, rather than with wells 36. Next, a series of small indentations is formed in the flat top surface of the gel. Referring to FIG. 23, a comb 240 is shown for making these indentations. A series of prongs 246 is formed at regular intervals with spaces 244 between each set of prongs. The comb 240 is inserted into the top of the gel cassette so that the prongs 246 just contact the top surface and form indentations a few thousandths of an inch thick. Samples of the material to be analyzed are then dropped into the areas corresponding with spaces 244 between each prong. Providing two prongs 246 between each sample area increases the isolation between the samples and makes it easier for an operator to distinguish between adjacent wells.

To make comb 240, prongs 246 are formed by punching or otherwise cutting a thin sheet of plastic 248 whose thickness is equal to the spacing between front and back plates 10 and 12 and whose length is equal to the distance between the inside monofilament side spacers 40. A second piece of plastic 250 is securely attached to one surface of plastic piece 248. The increased thickness provided by plastic piece 250 allows the comb to be aligned vertically within the cassette by placing the top or bottom edge of piece 250 on the top of back plate 12. The distance between the top of piece 250 and the top of piece 248, denoted A in FIG. 23, is very slightly smaller than the distance between the bottom of edge of piece 250 and the bottom of prongs 246, denoted as dimension B in FIG. 23. This allows the top surface of the gel to be formed by putting comb 240 into the gel cassette in an orientation upside down from that shown in FIG. 23. The flat top edge of comb 240 then forms a flat surface on the top of the gel material. After the gel has polymerized, comb 240 is reversed and inserted with prongs 246 facing the top of the gel surface. The comb is inserted until it is stopped by spacer 250, at which point the prongs 246 are barely penetrating the top surface of the gel. In this manner, the indentations may be formed very precisely in the top surface of the gel material.

The configuration of such a system is illustrated in FIGS. 5 and 6. In FIGS. 5 and 6, a plurality of detectors 110 are located behind the lower portion of the gel cell. Each detector receives radiation emerging through an associated collimator 112. Collimators 112 are integrally formed as a piece of the rear glass plate 12, as discussed in more detail below. As the radio-labelled molecule fragments travel downwardly from each of the wells 36 under the influence of the electric field, they will pass the corresponding collimator 112 and detector 110 at a time determined by the molecule size and resulting diffusion speed. By electronically detecting the passage of these molecular fragments an automatic analysis of the material may be performed. While automatic detection systems for performing analysis of electrophoresis diffusions have been proposed in the past, their effectiveness has been significantly limited due to the variations in the diffusion lanes and diffusion speeds which have been typical of prior art electrophoresis gel cassettes. The accuracy of the diffusions in the present invention makes such an automatic detection system much more practicable.

Additionally, the present invention may incorporate a collimator and detector system with advantages over prior art methods that further enhance the accuracy of the analysis.

Nucleic acid electrophoresis diffusion frequently use molecule segments which have been radio labelled. Phosphorus 32 is the isotope most frequently used for such radio-labelling. Other isotopes may also be used. These isotopes are typically of lower energy than phosphorus 32, and the considerations discussed below are consequently more important.

Phosphorus 32 is a beta emitter having an energy distribution which is centered around 600 keV. Most of these particles are of low enough energy to be blocked by the materials from which the front and back plates 10 and 12 are made. For example, a thickness of glass of 0.050" will absorb half the emission of a phosphorus 32 labelled molecule. Thus, the radiation cannot be detected efficiently through the thickness of the gel cell plates.

Figures 16, 17A, 17B, 18, 21:
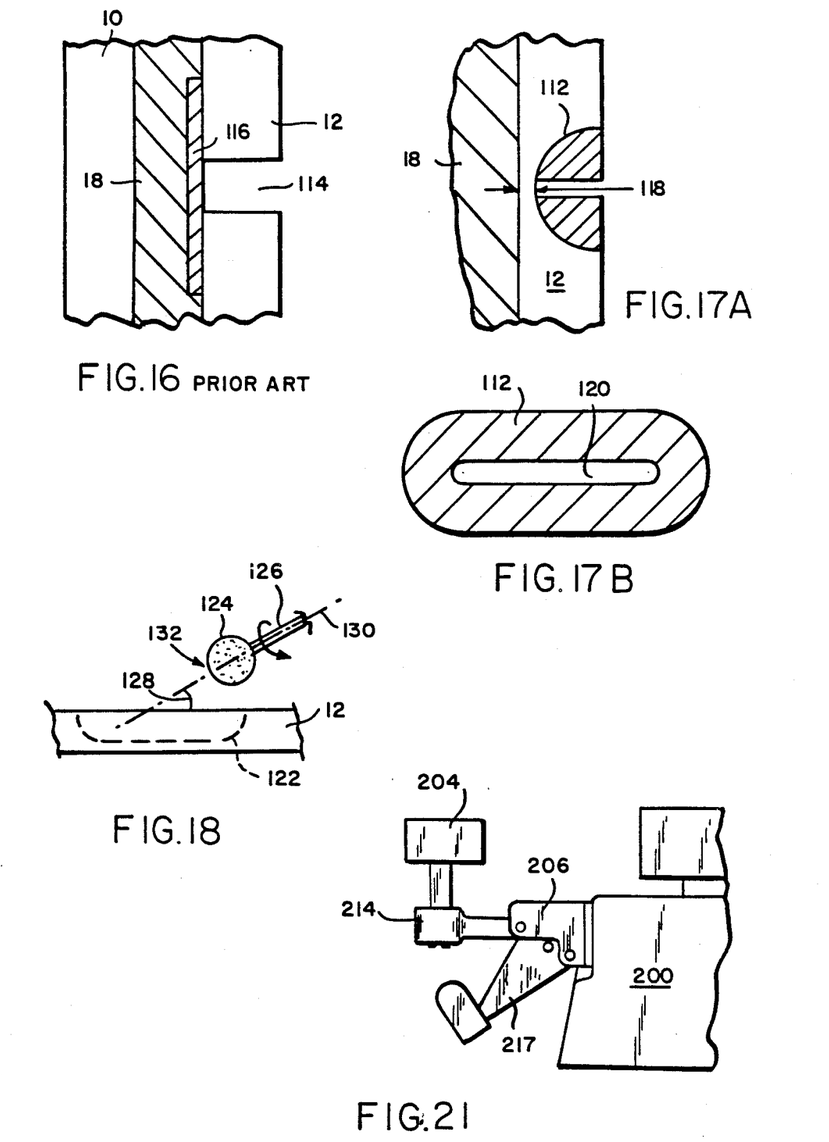

In prior art systems which have attempted to provide automatic detection of radio-labelled molecules, a groove has been formed which goes completely through the glass plate to allow the beta particles to be detected-. Referring to FIG. 16, a typical prior art method of allowing radio emissions to escape from the gel cell is shown.

In FIG. 16, an opening 114 is formed which extends entirely through the front or rear plate 10 or 12. The opening is then sealed with a strip of mylar or PET film glued to the glass over the opening 114. While this allows the emissions from radio labelled molecules to escape, it introduces undesirable distortions into the electric field. The thickness of film 116 is approximately 0.002" or greater. The thickness of the gel layer 18 is on the order of 0.010 to 0.020". The protrusion of the nonconductive film 116 into the gel layer 18 will significantly distort and affect the electric field in the vicinity of the slot 114.

In the present invention, a groove for each of the collimators 112 is ground most of the way through the rear glass plate 12. The groove is part-circular in cross section in order avoid stress concentration points. The groove is ground to a depth in the glass such that the thickness of the glass is approximately 0.005" thick at the bottom of the groove. This would correspond to the thickness indicated by the dimension 118 in FIG. 17A.

A metal collimator is then glued into place in the groove. Collimator 112 provides two functions. First, it serves to collimate the radiation from the radio labelled molecules to provide better resolution for the detector. Second, it reinforces the glass to add strength in the area where the glass has been ground down to a thin section to allow the radiation to be detected. As shown in FIG. 17A, the cross section of the collimator is part-circular in shape. FIG. 17B is a back view of the collimator and shows that it is oblong in shape having semi circular ends. A slot 120 extends through the collimator to allow the radio emissions to escape. The exact configuration of slot 120 may be varied depending upon the sensitivity of the detector, the resolution desired, and other factors. Various different collimator configurations are known in the art, and the configuration for slot 120 may be selected from such designs. In the preferred embodiment, collimator 112 is formed of kovar or tungsten, both of which have a coefficient of thermal expansion which is very close to that of the glass material from which the glass plate 12 is formed. Lead or brass or copper may also be used.

The collimator groove may be formed in the rear glass plate 12 in the following manner. In FIG. 18, glass plate 12 is shown with the outline of the desired groove denoted by dotted line 122. A spherical abrasive ball 124 is attached to a shaft 126 and rotated about its axis, denoted by line 130. Typically, the abrasive ball 124 is covered with a hard abrasive material, such as diamond dust. It is essential that the axis of rotation of the abrasive ball 124 be maintained at an angle 128 to the surface of the glass.

There is a "dead spot" 132 on the end of the abrasive ball 124 where the axis of rotation 130 intersects the ball surface. The rotation and abrasive action of the ball in this area is very small. It is desirable to prevent this spot from exerting significant pressure on the glass plate 12, since the dead spot 132 and its vicinity have little rotation and minimal abrasive grinding occurs in this area. Maintaining the abrasive ball in an orientation such that the dead spot 132 does little or no grinding of the glass surface in forming the groove 112 is essential to avoid breaking the glass. In the preferred embodiment, the diameter of ball 124 is 0.375", and angle 128 should be in a range of 45 degrees to 60 degrees. To form groove 122, the ball is lowered to full depth in the glass and then moved horizontally in one cut. To aid cooling and chip removal, a fixture is attached to the top of the glass to maintain the ball and machined section of the glass immersed in oil. The result is a oval groove having semi-circular ends into which the collimator shown in FIG. 17B may be inserted and glued.

Referring to FIG. 6, the radiation detector 110 should be located as closely as possible to collimator 112. This may cause undesirable thermal gradients in the gel 118 if the detector is mounted in such a way as to act as a heat shunt. These thermal gradients will adversely affect the diffusion of the radio labelled molecules.

The gel cassette typically operates at a temperature on the order of 50 to 60 degrees centigrade due to the heating of the gel caused by current flowing through the gel as a result of the electric potential applied across the gel. A detector or any other structure in contact with the rear glass plate 12 or collimator 112 may conduct heat to or away from the glass and may produce undesirable thermal gradients. For example, structures for mounting and positioning the gel cassette may significantly perturb the thermal equilibrium of the gel. Prior art cassette systems have used water jackets in an attempt to maintain even temperatures throughout the gel.

It has been found that the thermal equilibrium of the gel cassette may be best maintained by embedding the radiation detector 110 in a thermally conductive plate which extends substantially over the entire area of the rear plate 12 of the gel cassette. In FIG. 6, a plate 134 is shown which extends from the top of the gel cell to a location well below the point where collimator 112 is inset into rear plate 12. Plate 134 extends sideways the entire width of the gel cell. The primary requirement of plate 134 is that it have a high thermal conductivity, and aluminum is the preferred material. The gel cassette is located so that plate 134 contacts the rear of glass plate 12 over as much of its area as possible. This ensures that thermal equilibrium is maintained in the gel. Plate 134 is on the order of 1" thick, and it should be thermally isolated from all parts of the system except for the gel cassette. The bottom of reservoir 140 is supported by the top edge of the plate, and a bottom support piece 135 may be attached to the bottom edge of back plate 12 to aid positioning the cassette.

The method by which top reservoir 20 is attached to the gel cassette may affect the performance of the gel cassette. In prior art gel cassettes, such as that shown in FIG. 2, a structure 22 which forms the rear and side walls of the top reservoir 20 is typically clamped to the rear of the gel cassette. Sealing between the structure 22 and gel cassette plates is accomplished by means of a tubular gasket 28. Tubular gasket 28 requires that pressure be applied perpendicular to the surfaces of the glass plates not only along its sides but also in the middle of its top edge. Frequently, this pressure will bend or warp the glass plate resulting in distortion in the electric field within the gel material 18.

Figure 15A:
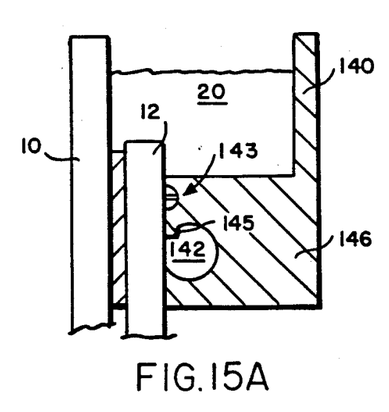

The present invention includes a novel method of attaching a top reservoir to the gel cassette. Referring to FIG. 6, the present invention includes a structure 140 which provides the reservoir rear and side walls. Its attachment to the gel cassette and the material from which it is made, however, differ significantly from prior art structures. FIG. 15A shows in more detail the configuration of the reservoir in the present invention. FIG. 15A is taken along the same section line in FIG. 5 as is FIG. 6. In FIG. 15A, the reservoir structure 140 is made from a resilient material, such as molded rubber. A bar 142 is attached to the outside face of rear glass plate 12 along the top edge, as shown in FIG. 15A. In the preferred embodiment, bar 142 is formed of a glass rod which has a flat ground on one side thereof, and the flat is glued to glass plate 12. Reservoir 140 has an opening molded into it which matches rod 142. The reservoir is pressed over the retaining rod 142 to maintain it in place. A sealing lip 143 may be provided along the top of the reservoir to ensure an electrolyte-tight seal. A small right angle notch 145 may also be provided at the top of rod 142 to provide further sealing and retention capabilities. Due to the resilient material from which reservoir 140 is made, it will seal along the back surface of plate 12 without requiring gaskets and clamps. Rod 142 additionally provides stiffening across the horizontal extent of the gel cassette which aids in resisting warpage.

Figure 15B:
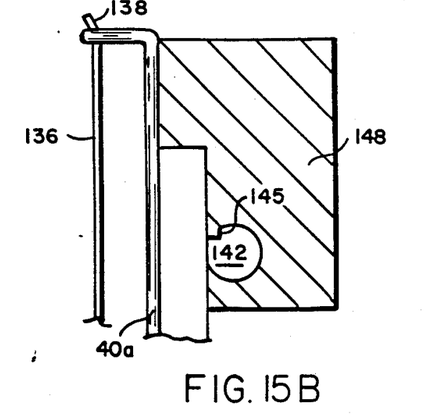

The side seal of the reservoir structure 140 is shown in FIG. 15B, which is a cross section taken along the line 15B—15B in FIG. 5. FIG. 15C is a top view of the reservoir which includes the cross section shown in FIG. 15B. A side wall 148 of the reservoir extends over the back of rear plate 12 and contacts the front glass plate 12 on either side of outside spacer 40a.

The usefulness of the above described gel cassette is enhanced by the method and apparatus discussed below for filling the cassette with gel material. As explained above, current methods of filling gel cassettes require considerable training and skill in order to produce an acceptable gel layer having uniform thickness and no discontinuities, such as would result from bubbles or dust particles in the gel layer. It has also been found the method described below of injecting gel into the cassette results in a more uniform thickness in the gel layer, compared with prior art methods, resulting in enhanced performance and accuracy.

Figures 19, 20, 22:
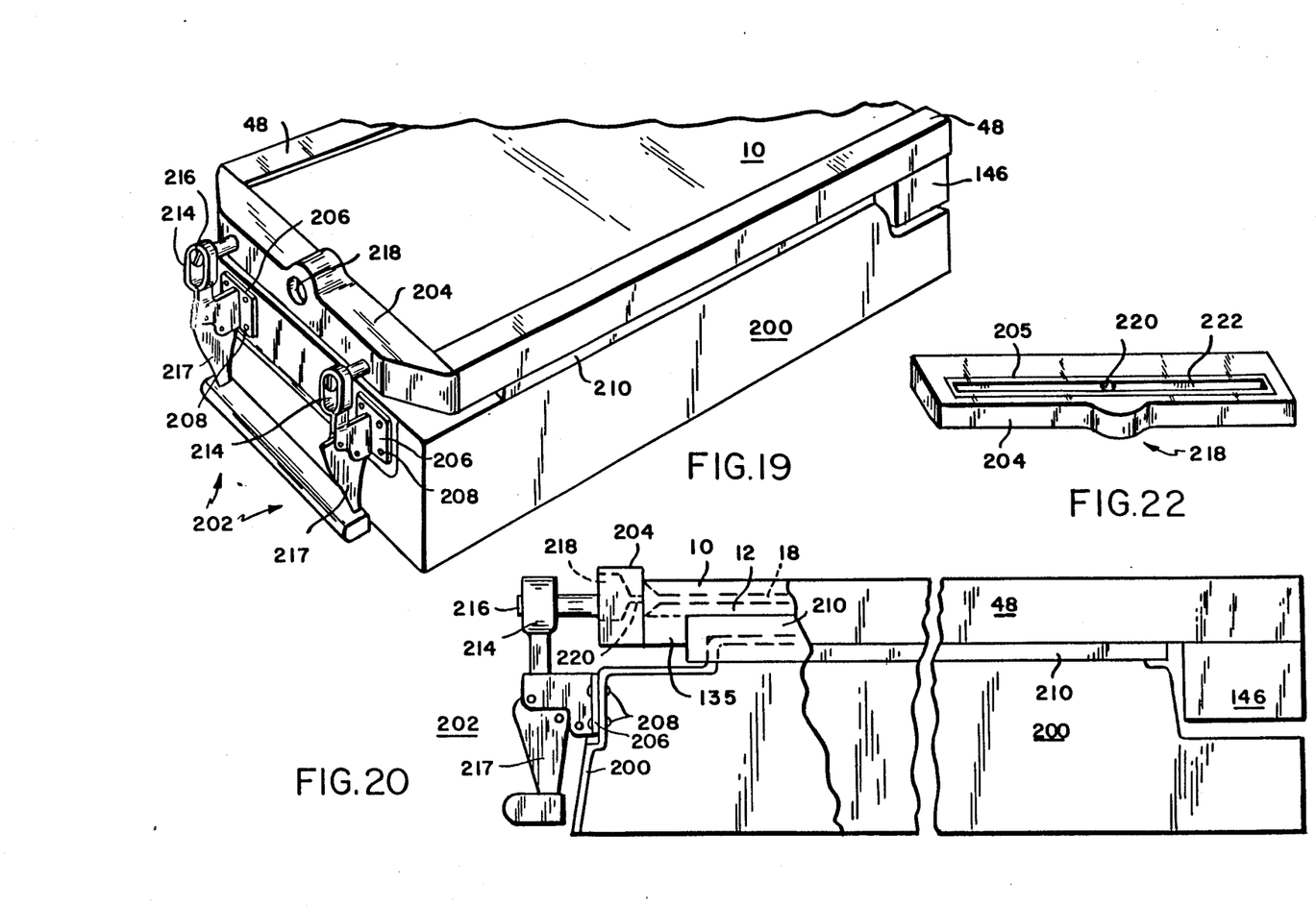

Referring to FIG. 19 an apparatus is shown in perspective view for injecting gel into the novel cassette described above. It should be appreciated that the following method and apparatus for filling gel cassettes are also applicable to prior art gel cassettes, such as that shown and explained in connection with FIGS. 1-4 above. FIG. 20 is a side view of the apparatus with certain sections exposed in a cut-away portion.

The filling apparatus includes a base member 200 which serves to support the cassette in a horizontal position as described in more detail below. A mechanism, showing generally at 202, is provided to position and clamp to the bottom of the gel cassette a rigid filling manifold 204 into which a resilient rubber sealing strip 205 is inserted. Manifold 204 serves to seal the bottom of the cassette while it is being filled with gel and also provides a passage way or manifold through which gel is injected between the front and back glass plates of the cassette.

Base 200 may be made from molded plastic or other suitable material. The clamping mechanism 202 is attached to base 200 by means of bolts 208 which pass through holes in mounting plates 206 of the clamping mechanism and which screw into corresponding threaded holes or bolts in base 200. The holes in mounting plates 206 are slightly oversized so that the position of the clamping mechanism may be adjusted slightly, as described below.

A flat rigid plate 210 is mounted on top of base 200. In the described embodiment, plate 210 is formed of aluminum. Plate 210 is preferably the same size as the aluminum plate 134 shown in FIG. 6. The lateral block piece 135 may be attached to the bottom edge of the back plate 12 to provide a stop which abuts against the front edge of aluminum plate 210. When in position to be filled, as shown in FIGS. 19 and 20, the cassette has its back plate 12 resting on support plate 210. It is important that the top surface of support plate 210 be flat and horizontal for reasons discussed below.

Clamping mechanism 202 includes right and left pivoting support pieces 214 which are attached to the rigid manifold block 204, such as by screws 216 or other means. In operation, support piece 214 and manifold block 204 are pivoted out of the way, as shown in FIG. 21, to allow the gel cassette to be placed in position as shown in FIG. 20. Following that, the manifold block is moved into place against the edge of the gel cassette, and is held in place by means of locking cams 217. The dimensions of clamping mechanism 202 in block 204 are such that sufficient force is applied by the clamping mechanism through block 204 to the cassette to insure a gel-tight seal between the rubber insert 205 in block 204 and bottom edges of the front and back plates of the cassette. No more force than is necessary should be applied to avoid possible deformation of the cassette, especially the front and back plates 10 and 12.

Block 204 includes a large opening 218 in the side opposite the gel cassette. This opening is designed to fit an injector for injecting gel medium between the front and back plates of the cassette. In the preferred embodiment, the injector is in the form of a syringe which may be inserted into and locked into opening 218. A small hole 220 through the rubber insert 205 of rigid manifold 204 aligned with a hole in the rigid manifold block 204. The gel medium injected by the syringe or other device flows through hole 220 and into the opening 18 between front and back plates 10 and 12. The surface of the rubber insert 205 in block 204 facing the cassette should be flat, except for a groove 222 which may extend for the width of the cassette to aid the filling of the buffer zones 68 of the cassette.

The rubber insert 205 of rigid manifold block 204 should be stiff enough to insure that a secure contact is maintained between itself and the bottom edge of the gel cassette along its length, and should also be resilient enough to provide a seal which will not allow gel material or air to pass. Silicone rubber is used for insert 205 in the described embodiment. A positive locking mechanism between the injector and the manifold is desirable. In the preferred embodiment which uses a conventional syringe to inject gel medium, a Luer fitting is provided at the end of opening 218, which mates with a matching fitting on the syringe.

The use of this system for filling a gel cassette has many advantages over prior art methods. First, it is easier to maintain a smooth bottom surface on the gel than when a cassette is filled from the top with the bottom taped as has been previously done. Second, an operator may carefully watch the gel material filling the gel cassette as it is being injected. Air bubbles, dust particles, or other causes of imperfections in the gel can be observed. If this occurs the gel material may be pulled back into the syringe by pulling on the plunger, and the affected area may be refilled. This is particularly useful when air bubbles are formed, since these bubbles may well be eliminated when the area is refilled.

Additionally, the procedure described above provides a gel layer 18 between front and back plates 10 and 12 which is more uniform in thickness than can be achieved by many prior art methods. Typically, prior art gel cassettes of the type shown in FIG. 1 are filled by sealing the bottom of an assembled gel cassette and pouring the gel material into the top of the cassette while the cassette is in a vertical or near vertical position. This procedure is much more prone to result in air bubbles and dust particles within the gel layer. If such imperfections are noticed during the pouring of the gel layer, the gel material must be moved around by tilting the entire cassette until the imperfection is removed. This is in contrast with the present invention in which such defects can frequently be eliminated by sucking some or all of the liquid gel solution back into the filling syringe and then reinjecting the gel.

The prior art method of filling a vertical cassette also results in a slight bulging outward of the front and back plates 10 and 12 due to hydrostatic pressure resulting from the weight of the gel material. This effect is more pronounced at the bottom of the gel cassette where the hydrostatic pressure is greatest. When using the novel filling method described, no such hydrostatic pressure is applied to the plate, since the cassette is filled in a horizontal position with substantially the entire surface of back plate 12 supported by the aluminum support piece 210.

From the above discussion, it should be apparent that there are essentially no bending forces on bottom plate 12. The only forces acting on bottom plate 12 during the filling operation are compressive forces resulting from the weight of the gel material 18 squeezing the rear glass plate 12 between the weight of the gel material 18 and support plate 210. These forces will not produce any appreciable deformation in glass plate 12.

Since the gel layer 18 will change from a liquid to a solid state after the gel cassette has been filled, little or no hydrostatic pressure is applied to front and back plates 10 and 12 by the solidified gel material when the cassette is moved to a vertical position. Because of this, back plate 12 can be made extremely thin, and may even be thinner than front plate 10, which must be thick enough to support its weight without bowing during the filling operation. A thinner rear plate 12 results in a smaller separation between the radio-labelled molecules and detectors 110. This results in a higher angle of acceptance of radiation emitted by the radio labelled molecules, and effectively increases the sensitivity of detectors 110. In the preferred embodiment, front plate 10 is 3/16 inch thick and rear plate 12 is 1/16" thick for a cassette with dimensions on the order of eight by twelve inches, a 3/16 inch thick front plate will bend a negligible amount under gravitational forces. The 1/16 inch front plate would bow out approximately one thousandth of an inch from the hydrostatic forces produced by conventional filling technique wherein the cassette is filled in a vertical position.

FIG. 22 illustrates the face of block 204 and rubber insert 205 which face the gel cassette. The large opening 218 into which a filling syringe fits is on the bottom of the block and is not shown in FIG. 22. The syringe seals against the back of the rubber insert so that its orifice connects directly to a small opening 220 in the rubber insert 205 which opens into longitudinal groove 222. The ends of groove 222 are closed by means of groove side walls which are integrally molded into rubber insert 205. Groove 222 should extend to approximately ⅛ the distance between the dual monofilament spacers on each side of the gel cassette. Groove 222 has been found to allow the gel materials to flow better resulting in a more even bottom surface for the gel layer, in addition to enhancing the filling of the buffer zones 68 between the monofilament spacers. In the preferred embodiment, the width of groove 222 is approximately 0.060", which is approximately six times the plate separation.

To assemble and fill a cassette in accordance with the present invention, the following steps should be carried out. First, the front and rear plates should be cleaned and silanized thoroughly. The monofilament spacing material is then cleaned and assembled to the top plate 10. Next, the bottom plate assembly with the reservoir attached is positioned on the filling apparatus, being aligned by the aluminum plate 210. Next, dust should be removed from both the top and bottom plates, and the top plate immediately assembled to the bottom plated with the bottom edge of the top plate slightly above the bottom edge of the rear plate. The side clamps 48 are then put into place without tightening the locking rods.

Next, bottom filling block 204 is moved into place against bottom plate 12 and locked into place with locking cam 218. If necessary, a small amount of grease ma be put onto the front face of block 204 to aid in providing a good seal. This is typically only necessary along the outside edges of the seal. The front plate 10 is then slowly moved downward until it just touches the rubber insert of block 204 to provide a seal, and the locking rods of side clamps 48 are twisted into the locked position.

A syringe is then filled with liquid gel solution, being careful to remove all air bubbles from the syringe. In the present embodiment, a 30cc syringe is used. The syringe is then inserted into its receptacle 218 in block 204. The syringe plunger is slowly depressed to fill the cassette until the gel solution overflows the cassette at the top. The gel material, although liquid, has sufficient surface tension to fill up the entire area between the front and glass plates without gaps as the syringe plunger is depressed. After the cassette has been completely filled, a comb with the desired well configuration is inserted into the top of the gel material. If necessary, the plunger is depressed further until the channels at either side of the cassette between the monofilament spacers are completely filled. After the cassette has been completely filled, the filler block is swung out of the way to remove pressure of the plates. The gel is allowed to polymerize to a solid before the cassette is removed from the filling fixture, and in particular before the cassette is moved from its horizontal position.

There has been described a novel system for making a gel cassette and for performing an automated electrophoresis diffusion which has advantages over methods and devices previously used. It should be apparent that modifications to the preferred embodiment disclosed herein above will be made by those of ordinary skill when using the teachings of the present invention in different applications and situations. Accordingly, the invention should not be deemed to be limited by the particular embodiments utilized above to explain the features of the invention. Rather, the invention should only be interpreted in accordance with the following claims.

What is claimed:

1. An electrophoresis cassette, comprising:
   a first flat plate having two sides which are substantially parallel to each other and having top and bottom edges;
   a second flat plate having two sides which are substantially parallel to each other and having top and bottom edges;
   means for holding the first and second plate in a fixed relationship with each other wherein the sides of the first plate are substantially parallel to the sides of the second plate and the opposing faces of the plates are separated by a predetermined distance to form a space therebetween, the sides, bottom edges and top edges of the plates corresponding to the sides, bottom edge and top edge of the assembled cassette;
   the space between the plates being adapted for filling with a gel in which an electrophoresis separation may be performed;
   the means for holding including;
   means for providing a line contact seal between the first and second plates along each of the sides of the cassette immediately adjacent to said space adapted to be filled with a gel, and including at least one elongate sealing piece along each side of the space which serves both to provide said line contact seal and to maintain the separation between the plates at said predetermined distance; and
   means for clamping the two plates together along the side thereof.

2. The electrophoresis cassette of claim 1 wherein the means for providing a line contact seal includes on each side of the space between the plates, a first piece of monofilament located between the two plates and substantially parallel to the sides of the plates, which is compressed between the plates by the means for clamping to provide a line contact seal between the monofilament and each plate.

3. The electrophoresis cassette of claim 2 wherein the means for holding further includes on each side of the space between the plates, a second piece of nylon monofilament located between the two plates and substantially parallel to the sides of the plates and the first piece of monofilament, which is compressed between the plates by the means for clamping to provide a second line contact seal between the second piece of monofilament and each plate, thereby defining a buffer space between the first and second pieces of monofilament on each side of the space.

4. The electrophoresis cassette of claim 3 wherein each of the plates is made of glass.

5. The electrophoresis cassette of claim 1 wherein the bottom edge of at least one of the flat plates is beveled, the bevel facing toward the space between the plates fillable with the gel, whereby a wider section of gel running along the bottom side of the plate is provided having a lower resistance per unit length than the gel between the plates above the bottom edge bevel.

6. The electrophoresis cassette of claim 1 wherein the means for clamping includes a clamp affixed to each side of the two plates, each clamp comprising:
   means for applying pressure to the outside surfaces of each of the glass plates along the line contact seal, which pressure is substantially continuous and constant along the length of the line contact seal.

7. The electrophoresis cassette of claim 1 wherein the means for clamping includes a clamp affixed to each-side of the cassette, each clamp comprising: a long, generally U-shaped channel section open along one side thereof;
   a long, resilient piece having a lengthwise opening therethrough which has a cross section having a larger axis and smaller axis, the resilient piece having a flat surface along one side which abuts against one of the plates, the larger axis of the opening being approximately parallel to the flat surface;
   a long rod which has a cross-section having a larger axis and a smaller axis, and which may be inserted into the lengthwise opening when the larger axis of the opening is generally parallel to the larger axis of the rod;
   the resilient piece and the U-shaped channel being sized so that the opening along the channel section side may receive therein the resilient piece and the assembled plates and so that clamping pressure is applied to the plates to hold them together when the long rod is inserted into the lengthwise opening and rotated so that its smaller axis is generally perpendicular to the smaller axis of the opening.

8. The electrophoresis cassette of claim 1 further including:
   a reservoir container adapted to be attached to the top of the assembled plates to hold an electrolyte solution; and means for attaching the reservoir to the assembled plates without applying a pressure to the plates which would tend to deform the plates.

9. The electrophoresis cassette of claim 8 wherein the means for attaching includes:
   a first piece attached to the outside surface of one of the plates near the top edge thereof substantially parallel to said top edge and extending across substantially the entire width of the plate;
   mounting means, for attaching the reservoir to the first piece and for providing a seal between the reservoir and the first piece, including a resilient section in said reservoir having an opening therein adapted to fit closely over said first piece.

10. The electrophoresis cassette of claim 1 further including:
    a plurality of cavities formed in the outside surface of one of said plates, said cavities extending into but not through the plate;
    a plurality of collimators, each associated with and implanted within one of said plurality of cavities.

11. The electrophoresis cassette of claim 10 wherein the collimators are formed of kovar.

12. The electrophoresis cassette of claim 10 wherein the collimators are formed of a material selected from tungsten, lead, brass, or copper.

13. The electrophoresis cassette of claim 1 wherein the means for providing a line contact seal includes a long, slender sealing piece having a substantially constant cross-section throughout its length.

14. The electrophoresis cassette of claim 13 wherein the cross sectional area of the sealing piece is circular.

15. The electrophoresis cassette of claim 14 wherein the sealing piece is made of nylon.

16. The electrophoresis cassette of claim 1 wherein the means for providing a line contact seal includes two sets of at least two long, slender sealing pieces having a substantially constant cross-section throughout their length and located between the two plates, one set located along each pair of edges of the assembled plates, whereby multiple line contact seals are provided along each edge of the assembled cassette.

17. The electrophoresis cassette of claim 16 wherein the cross-sectional area of the sealing pieces is circular and wherein the sealing pieces are made of nylon.

18. The electrophoresis cassette of claim 17 wherein the means for clamping includes a clamp affixed to each side of the cassette, each clamp comprising:
    means for providing pressure to the outside surfaces of each of the glass plates along the point contact seals, which pressure is substantially continuous and constant along the length of the point contact seals.

19. The electrophoresis cassette of claim 18 wherein the bottom edge of at least one of the plates is beveled, the bevel facing towards the space between the plates filled with gel, whereby a wider section of gel running along the bottom edge of the cassette is provided.

20. The electrophoresis cassette of claim 19 further including:
    a reservoir container adapted to be attached to the top of the assembled plates to hold an electrolyte solutions; and
    means for attaching the reservoir to the assembled plates without applying a pressure to the plates which would tend to deform the plates, including:
    a first piece attached to the outside surface of one of the plates near the top thereof and generally parallel to the top edge; and mounting means, including a resilient section in said reservoir having an opening therein adapted to fit closely over said first piece, for attaching and providing a seal between the reservoir and the first piece.

21. The electrophoresis cassette of claim 20 further including:
    a gel filling the space between the plates;
    a plurality of wells, for receiving a sample to be electrophoretically separated, formed in the top edge of the gel and extending between the innermost seals along each side of the cassette, the wells comprising a plurality of first indentations each extending the same depth into the gel top surface; and
    an additional indentation on each side of the plurality of first indentation located between the outermosts indentation and the adjacent seal on each side, the bottom of said additional indentations extending to the adjacent seal and having a depth from one-half toone times the depth of the wells.

22. The electrophoresis cassette of claim 1 further including:
    a gel filling the space between the plates;
    a plurality of wells, for receiving a sample to be electrophoretically separated, formed in the top edge of the gel and extending between the contact seals along each side of the cassette, the wells comprising a first plurality of indentations each extending the same depth into the gel top surface; and
    an additional indentation of each side of the first plurality of indentation located between the outermost indentation and the adjacent seal on that side, the bottom said additional indentations extending to the adjacent seal and having a depth from one-half to one times the depth of the wells.

23. An electrophoresis system, comprising:
    an electrophoresis cassette as set forth in claim 1;
    top reservoir means attached, to the top edge of the assembled cassette for containing an electrolyte solution in which the top edge of the cassette is submerged;
    bottom reservoir means for containing a second electrolyte solution into which the bottom edge of the cassette is submerged;
    means for mounting the cassette, including:
      a mounting plate having a high thermal conductivity and at least one flat surface;
      means for mounting the assembled cassette to the mounting plate so that substantially all of the outside surface of said first plate is in contact with the mounting plate flat surface and so that the bottom edge of the cassette extends into the bottom reservoir means; and
    means for applying an electric potential between the electrolyte in the top reservoir means and the electrolyte in the bottom reservoir means.

24. The electrophoresis cassette system of claim 23 further a plurality of detectors for detecting radiation, said detectors being mounted in said mounting plate so that they are flush with the flat surface thereof.

25. The electrophoresis cassette system of claim 24 further including:

a plurality of cavities formed in the outside surface of said first plate, said cavities extending into but not through the plate and being located so that they are opposite the plurality of detectors in the mounting plate;

a plurality of collimators, each associated with and implanted within one of said plurality of cavities.

26. The electrophoresis cassette system of claim 25 wherein the mounting plate is composed primarily of aluminum.

27. The electrophoresis cassette system of claim 26 wherein the flat plates are formed of glass.

28. The electrophoresis cassette of claim 27 wherein the collimators are formed of a material selected from kovar, tungsten, brass, lead or copper.

29. The electrophoresis cassette system of claim 23 wherein the mounting plate is composed primarily of aluminum.

30. The apparatus of claim 2 wherein the monofilament is made of nylon.

31. The apparatus of claim 3 wherein the monofilament is made of nylon.

32. In an electrophoresis cassette of the type having first and second parallel plates separated by spacers extending along two sides thereof to form a thin cavity between the plates bounded on the sides by said spacers and open on the top and bottom edges of the cassette, the cavity being filled with said gel, the improvement comprising a bevel formed along the bottom edge of at least one of the plates, the bevel facing towards the cavity between the plates, whereby a thicker section of gel may be provided in said cavity along the bottom edge of the cassette.

33. The improved cassette of claim 32 further comprising a second bevel formed along the bottom edge of the second one of the plates, the bevel facing towards the cavity between the plates.

34. In an electrophoresis cassette of the type having first and second parallel plates separated by side spacers extending along two sides thereof to form a thin cavity between the plates bounded on the sides by said spacers and open on the top and bottom edges of the cassette, the cavity being filled with gel, and including a plurality of wells formed in the top edge of the gel for receiving samples to be electrophoretically separated, the wells comprising a first plurality of indentations each extending the same depth into the gel top surface, the improvement comprising:

an additional indentation on each side of the plurality of first indentation and located between the outermost well on each side and the side spacer on that side, said additional indentations having a depth from one-half to one times the depth of the wells, the bottoms of said additional indentations extending all the way to the side spacers.

35. The improved cassette of claim 34 wherein the well and additional indentations are all rectangular in shape.

36. An improved well-forming comb for use with an electrophoresis cassette of the type having first and second parallel plates separated by side spacers extending along two sides thereof to form a thin cavity between the plates bounded on the sides by said spacers and open on the top and bottom edges of the cassette, the cavity being filled with gel, the comb being inserted into the gel material from the top and including a plurality of projections to form in the top edge of the gel a plurality of wells for receiving samples to be electrophoretically separated, the wells being formed as a plurality of indentations each extending the same depth into the gel, the improvement comprising:

additional projections means on the comb for forming additional indentations between the outermost wells on each side and the side spacer on that side so that said additional indentations have a depth from one half to one times the depth of the wells and so that the bottoms of said additional indentations extend all the way to the side spacers.

* * * * *